United States Patent [19]

Thompson

[11] Patent Number: 5,635,216
[45] Date of Patent: Jun. 3, 1997

[54] MICROPARTICLE COMPOSITIONS CONTAINING PEPTIDES, AND METHODS FOR THE PREPARATION THEREOF

[75] Inventor: William W. Thompson, Indianapolis, Ind.

[73] Assignee: Eli Lilly and Company, Indianapolis, Ind.

[21] Appl. No.: 168,941

[22] Filed: Dec. 16, 1993

[51] Int. Cl.$^6$ .................................................... A61K 9/14
[52] U.S. Cl. .................................. 424/501; 514/2; 514/12
[58] Field of Search ................................. 424/422, 486, 424/489, 490, 497, 501; 514/2, 12

[56] References Cited

U.S. PATENT DOCUMENTS

| | | |
|---|---|---|
| 4,148,871 | 4/1979 | Pitt et al. . |
| 4,530,840 | 7/1985 | Tice et al. . |
| 4,542,025 | 9/1985 | Tice et al. . |
| 4,741,872 | 5/1988 | De Luca et al. . |
| 4,767,628 | 8/1988 | Hutchinson . |
| 4,962,091 | 10/1990 | Eppstein et al. ............................ 514/2 |
| 5,192,741 | 3/1993 | Orsolini et al. ............................ 514/4 |
| B1 4,767,628 | 7/1990 | Hutchinson . |

OTHER PUBLICATIONS

P. Couvreur and F. Puisieux, "Nano– and microparticles for the delivery of polypeptides and proteins", *Advanced Drug Delivery Reviews*, 1993, vol. 10, pp. 141–162 May–Jun.

Reza Arshady, "Microspheres and Microcapsules, a Survey of Manufacturing Techniques: Part III: Solvent Evaporation", *Polymer Engineering and Science*, Mid–Aug., 1990, vol. 30, No. 15, pp. 915–924.

H.. Jeffrey, et al., "The preparation and characterisation of poly(lactide–co–glycolide) microparticles. I: Oil–in–water emulsion solvent evaporation", *International Journal of Pharmaceutics*, 1991, vol. 77, pp. 169–175 Oct.

Hua–Pin Huang and Isaac Ghebre–Sellassie, "Preparation of microspheres of water–soluble pharmaceuticals", *J. Microencapsulation*, 1989, vol. 6, No. 2, pp. 219–225 Apr.–Jun.

D. Bodmer, et al., "Factors influencing the release of peptides and proteins from biodegradable parenteral depot systems", *Journal of Controlled Release*, 1992, vol. 21, pp. 129–138 Jul.

B. Mariette, et al., "Release of the GRF29NH$_2$ analog of human GRF44NH$_2$ from a PLA/GA matrix", *Journal of Controlled Release*, 1993, vol. 24, pp. 237–246 Jun.

B. Floy, et al., "Design of Biodegradable Polymer Systems for Controlled Release of Bioactive Agents", *Polymeric Delivery Systems*, American Chemical Society, 1993, pp. 154–167 (month unavailable).

V.J. Csernus, et al., "Release of peptides from sustained delivery systems (microcapsules and microparticles) in vivo", *Int. J. Peptide Protein Res.*, 1990, vol. 35, pp. 557–565 Jun.

R. Jalil and J.R. Nixon, "Microencapsulation using poly-(DL–lactic acid)I: Effect of preparative variables on the microcapsules characteristics and release kinetics", *J Microencapsulation*, 1990, vol. 7, No. 2, pp. 229–244 Apr.–Jun.

J.L. Grangier, et al., "Nanoparticles as carriers for growth hormone releasing factor", *Journal of Controlled Release*, 1991, vol. 15, pp. 3–13 Feb.

*Primary Examiner*—Jeffrey C. Mullis
*Attorney, Agent, or Firm*—Paul R. Cantrell; Kathleen R. S. Page

[57] ABSTRACT

A composition of polyester microparticles containing bioactive polypeptide agents and methods for preparing the composition and administering bioactive agents. The composition comprises biocompatible, biodegradable microparticles having a polyester matrix and from about 5% to about 25% by weight of a biologically active, water-soluble polypeptide dispersed throughout the matrix, the polypeptide selected from the group consisting of growth hormone releasing factor, synthetic analogs of growth hormone releasing factor, pharmacologically active fragment thereof and somatogenin. The method for preparing the composition includes dissolving polyester in an organic solvent; suspending a biologically active agent in the polyester solution; emulsifying the suspension into an aqueous medium in which the agent is insoluble and evaporating the solvent from the emulsion to produce microparticles. The method for administering a bioactive agent to an organism involves suspending the microparticles in a suitable liquid and injecting the organism.

6 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 76 amino acids
        ( B ) TYPE: amino acid
        ( D ) TOPOLOGY: linear     ( i i ) MOLECULE TYPE: protein (ix) FEATURE:
    (A) NAME/KEY: paramethylbenzoyl
    (B) LOCATION: 1
    (D) OTHER INFORMATION: acyl group (xi) SEQUENCE DESCRIPTION: SEQ ID NO:1:

| Gly | Ala | Asp | Ala | Ile | Phe | Thr | Asn | Asn | Tyr | Arg | Arg | Val | Leu | Thr | Gln |
|---|---|---|---|---|---|---|---|---|---|---|---|---|---|---|---|
| 1 | | | | 5 | | | | | 10 | | | | | 15 | |
| Leu | Ser | Ala | Arg | Arg | Leu | Leu | Gln | Asp | Ile | Leu | Ser | Arg | Gln | Gln | Gly |
| | | | 20 | | | | | 25 | | | | | 30 | | |
| Glu | Arg | Asn | Gln | Glu | Gln | Gly | Ala | Arg | Val | Arg | Leu | Gly | Arg | Gln | Val |
| | | 35 | | | | | 40 | | | | | 45 | | | |
| Asp | Ser | Leu | Trp | Ala | Asp | Gln | Arg | Gln | Leu | Ala | Leu | Glu | Ser | Ile | Leu |
| | 50 | | | | | 55 | | | | | 60 | | | | |
| Ala | Thr | Leu | Leu | Gln | Glu | His | Arg | Asn | Ser | Gln | Gly | | | | |
| 65 | | | | | 70 | | | | | 75 | | | | | |

MICROPARTICLE COMPOSITIONS CONTAINING PEPTIDES, AND METHODS FOR THE PREPARATION THEREOF

BACKGROUND OF THE INVENTION

1. Field of the Invention

The present invention relates generally to the field of biodegradable microparticles for the controlled release of biologically active agents therefrom. In addition, the present invention relates to a process for preparing polyester microparticles containing peptides which remain chemically stable, physically stable, and biologically active.

2. Background of the Invention

A variety of microencapsulation techniques have been used for years by the pharmaceutical industry to separate incompatible chemical entities, to convert liquids to free-flowing powder, to improve the dissolution rates and bio-availabilities of drugs, to protect the compounds from decomposition, and to mask unfavorable odor or taste. Another area to benefit from microencapsulation technology is the development of controlled-release formulations. Numerous carriers and encapsulation techniques have been evaluated and characterized. As a result, microcapsules with sustained-release properties have been successfully developed. However, most drugs that have been used in these microparticles have been relatively water-insoluble.

While water-insoluble compounds have inherent sustained-release properties when incorporated in a polymer matrix, and are relatively easy to encapsulate, preparation of sustained-release microcapsules of water-soluble pharmaceuticals poses a great challenge to pharmaceutical scientists. It is not surprising, therefore, that the literature provides little information on the microencapsulation of water-soluble drugs.

Peptide drugs are attracting increasing interest as their role in physiopathology becomes better understood, and because of progress in biotechnology and in conventional chemical synthesis. The development of DNA-recombination techniques has made these compounds available on a larger scale than in the past. However, peptides are generally characterized by a short biological half-life. This and other factors have led to the development of many new drug delivery systems, including the use of microparticles for the safe and controlled administration of peptides.

Microparticles are spherical polymeric particles ranging in size from greater than one micron up to 2000 microns. Microparticles include microcapsules in which the biological agent is uniformly confined within a cavity, and microspheres in which the agent is dispersed throughout the microparticle. Many processes can be used for the preparation of microparticles, including solvent evaporation, organic phase separation, interfacial polymerization, emulsion polymerization, and spray drying. However, only a few methods are acceptable for preparing peptide microparticles. The physicochemical properties of many peptides make their formulation difficult, and inactivation is possible during their incorporation into microparticles.

Numerous polymers have been used as matrices for microparticles, including polysaccharides, polyesters and nonbiodegradable synthetic polymers. Most methods for microencapsulation of peptides employ polyesters, especially poly(D,L-lactide-co-glycolide). The polyesters are desireable for this purpose because they are biodegradable or bioerodible, readily available, easily processed and non-toxic.

Microspheres of lactic and glycolic acids may be obtained conveniently by a solvent evaporation process which is, in spite of some limitations, compatible with the handling of numerous peptides. However, a major obstacle to the particulate formulation of peptides is the high water solubility of those molecules. The typical processes for microencapsulation are based on the affinity of the compound for the polymer or for the lipophilic phase of an emulsion. As a result, drug loadings for peptides have typically been less than 10% with the solvent evaporation processes used in the past.

Prior art efforts to overcome these problems have thus far included the use of a double emulsion technique, and of a phase separation process induced by the addition of a silicone oil. However, there has remained a need for methods for the preparation of biodegradable microparticles incorporating peptides which are stable and active, and which pay out at desired rates over time.

SUMMARY OF THE INVENTION

Briefly describing one aspect of the present invention, there is provided a composition including biocompatible, biodegradable microparticles having a polyester matrix and from about 5% to about 25% by weight of a biologically active, water-soluble polypeptide dispersed throughout the matrix. In another aspect of the invention, microparticles containing biologically active peptides are prepared by dissolving polyester in an organic solvent; suspending a biologically active agent in the polyester solution; emulsifying the suspension into an aqueous medium in which the agent is insoluble and evaporating the solvent from the emulsion to produce microparticles. One advantage of the present invention is the ability to conveniently prepare microparticles which have a relatively high ratio of peptide to polyester. In a still further aspect, there is provided a method for administering a bioactive agent to an organism which involves suspending the microparticles in a suitable liquid and injecting the organism.

It is an object of the present invention to provide microparticles incorporating biologically active agents, e.g., peptides, in a biodegradable and biocompatible matrix.

A further object of the present invention is to provide methods for the preparation of microparticles which contain peptide agents, which methods achieve up to 25% loading of the agents.

It is another object of the present invention to provide microparticles which contain peptide agents which are released under in vivo conditions at sustained, predictable rates.

A further object of the present invention is to provide methods for the preparation of microparticles containing peptide agents, which methods do not result in the destabilization, destruction or inactivation of the peptides.

It is another object of the present invention to provide microparticles, and methods for the preparation thereof, which permit modification of the release characteristics of the microparticles by adjustment of the matrix properties.

These and other objects, advantages and features are accomplished according to the compositions and methods of the following description of the preferred embodiment of the present invention.

DESCRIPTION OF THE PREFERRED EMBODIMENT

For the purposes of promoting an understanding of the principles of the invention, reference will now be made to the preferred embodiments thereof, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides microparticle formulations which comprise polyesters as the supporting matrix and peptides as the contained, biologically active agents. The microparticles are prepared by a solvent evaporation technique which incorporates the peptides in a stable and active form. The microparticles are biodegradable, and afford a controlled, sustained release of the peptides. The rate of drug release is controlled by adjusting factors such as the degree of peptide loading, molecular weight of the biodegradable polymer, and in certain instances the ratio of copolymer components. The microparticles, and preparatory methods, of the present invention are distinctive from the prior art in providing formulations in which the peptides remain chemically stable, physically stable (conformation), and biologically active. The methods of the present invention also achieve a greater proportion of peptide to polymer than prior art solvent evaporation techniques for microparticles incorporating water-soluble polypeptides.

The microparticles of the present invention provide sustained release of the contained peptides. As a result of the method of preparing the microparticles, the biologically active compounds, e.g., peptides and the like, are entrapped in the polymer network during fabrication. The peptides are then released over time during the degradation of the matrix, and to a limited extent, by diffusion through the polymer network.

The release profile may be adjusted by appropriate choice or control of various parameters. For example, release characteristics will charge with the polymer composition, particularly the type and proportion of polymers; the molecular weight of the polymers; the weight-average molecular weight ($M_w$); the molecular weight range (or polydispersity) measured by the ratio of the weight-average molecular weight ($M_w$) to the number-average molecular weight ($M_n$) i.e. $M_w/M_n$; the size and shape of the microparticles; and the proportion of peptide to polymer, i.e., the loading.

The microparticles of the present invention may be prepared from polyesters, e.g., poly(D,L-lactide), poly(D,L-lactide-co-glycolide), poly(epsilon-caprolactone), polyaminoacids, poly(orthoesters), polyanhydrides, polyalkyl cyanoacrylates. Any polyesters which are biodegradable and/or bioerodible, and yield biocompatible materials upon degradation are contemplated.

The polylactides are especially preferred for use in accordance with the present invention. Polymeric materials for preparation of the microparticles are available commercially. The term polylactide is used in a generic sense to include polymers and mixtures of polymers of lactic acid alone, copolymers of lactic acid and glycolic acid and mixtures of such copolymers, and mixtures of such polymers and copolymers, the lactic acid being either in racemic or in optically active form. The term PLA/PGA is used herein to refer to the various copolymers of lactic and glycolic acids. The molecular weigh of the polymers ranges from about 29,000 Daltons to about 90,900 Daltons. The ratio of lactide units to glycolide units ranges from 100:0 to 50:50. For example, one PLA/PGA polymer used had a ratio of PLA to PGA of 85:15, an inherent viscosity of 0.58 dL/g, and a molecular weight of approximately 90,900 daltons. This particular polymer was obtained from Birmingham Polymers, Incorporate (BPI), and is prepared by ionic, ring-opening, addition polymerization of the respective cyclic dimers of lactic and glycolic acids.

Upon exposure to water, the polyesters degrade through hydrolysis of ester linkages to yield biocompatible products. For example, the preferred PLA/PGA polymers degrade to lactic acid and glycolic acid. The 85:15 PLA/PGA copolymer has been reported to have a biodegradation time of approximately 5 months, depending on surface area, porosity and molecular weight. Other blends of PLA/PGA have degradation times ranging from 2 months to 24 months. A 50:50 PLA/PGA polymer, which has alternately been used, has a reported degradation time of 2 months. Similarly, the other polyesters used in the present invention have suitable biocompatibility and degradation times.

The microparticles prepared in accordance with the disclosed methods are suitable for use in the administration of various peptide agents. An advantage of this invention is that it provides microparticles containing small, biologically-active polypeptides. Generally, peptides of molecular weights up to 10,000 daltons are called polypeptides, while peptides of molecular weights above 10,000 daltons are called proteins. In the past, the solvent evaporation technique for preparing microparticles has typically resulted in low loading of small water-soluble peptides due to the incompatibility of such peptides with this process. Typically, loadings of below 10% have been reported. Low loading of microparticles may not provide a proper dose. However, in spite of its limitations, the solvent evaporation procedure is preferred because of its ease and reliability. The methods of the present invention employ an aqueous medium in which the biological agent is insoluble, and the process results in microparticles having loading up to 25%. The present invention addresses the need for convenient methods to incorporate polypeptides into microparticles with loading of 5–25%.

The present invention provides microparticles containing water-soluble polypeptides such as somatogenin. Somatogenin (LY293404) is the name proposed to the United States Adopted Names Council (USAN) for a 4-methylhippuroyl (1) porcine GHRH (2–76)—OH, which is an analog of a natural porcine GHRH prohormone. This compound has a molecular weight of 8846.89 daltons and its molecular formula is $C_{379}H_{624}N_{127}O_{118}$. Methods for the preparation of somatogenin are described in U.S. patent application, Ser. No. 07/692,090, filed on Apr. 26, 1991, now abandoned and entitled "Superactive GRF Analogs". The structure of somatogenin is represented by the following, SEQ ID NO: 1

Gly.Ala.Asp.Ala.Ile.Phe.Thr.Asn.Asn.Tyr.Arg.Arg.Val.Leu.Thr.Gln.Leu.Ser.
1          5           10              15

Ala.Arg.Arg.Leu.Leu.Gln.Asp.Ile.Leu.Ser.Arg.Gln.Gln.Gly.Glu.Arg.Asn.Gln.Glu.
20          25              30              35

Gln.Gly.Ala.Arg.Val.Arg.Leu.Gly.Arg.Gln.Val.Asp.Ser.Leu.Trp.Ala.Asp.Gln.Arg.
40          45              50              55

Gln.Leu.Ala.Leu.Glu.Ser.Ile.Leu.Ala.Thr.Leu.Leu.Gln.Glu.His.Arg.Asn.Ser.Gln.
60          65              70              75

Gly.OH

COMPOSITION TABLE

| Ala | 7  | Gly | 5  | Pro | 0 |
|-----|----|-----|----|-----|---|
| Arg | 11 | His | 1  | Ser | 5 |
| Asp | 4  | Ile | 3  | Thr | 3 |
| Asn | 4  | Leu | 12 | Tyr | 1 |
| Cys | 0  | Lys | 0  | Trp | 1 |
| Glu | 4  | Met | 0  | Val | 3 |
| Gln | 11 | Phe | 1  |     |   |

The preparatory method of the present invention is demonstrated in the following examples. In general, the polymeric material is dissolved in a suitable organic solvent, e.g. methylene chloride or chloroform, and the bioactive, water-soluble peptide, e.g. somatogenin, is added thereto. Preferably, the somatogenin has been reduced in particle size by air milling. See U.S. Pat. No. 5,021,554, the pertinent portions of which are hereby incorporated by reference. The polymer solution/peptide suspension is preferably sonicated to primary particles size. The suspension is then emulsified into a suitable aqueous media in which the bioactive peptide is insoluble, preferably, phosphate buffered saline. The medium may contain a stabilizer such as poly(vinyl alcohol), sodium dodecyl sulfate, cetyltrimethyl ammonium bromide, methylcellulose or gelatin. Various excipients may be added to the above at concentrations up to about 10%. Excipients may include, for example, fatty acids, such as stearic acid, myristic acid, lauric acid, and preferably, palmitic acid. The solvent is allowed to evaporate with the consequent formation of the microparticles. The evaporation is preferably aided with stirring. The particles are collected, preferably by vacuum filtration. The particles may then be dried in a desiccator under vacuum, and sieved to size appropriate for use.

This invention is applicable to polypeptides, and the following list, which is not intended to be exhaustive, is indicative of polypeptides which may be employed in the formulations of this invention: growth horone releasing factor, somatogenin, oxytocin, vasopressin, adrenocorticotrophic hormone (ACTH), epidermal growth factor (EGF), prolactin, luliberin or luteininzing hormone releasing hormone (LH-RH), transforming growth factor, insulin, somatostatin, glucagon, interferon, gastrin, tetragastrin, pentagastrin, urogastrone, secretin, calcitonin, enkephalins, endorphins, angiotensins, renin, bradykinin, bacitracins, polymyxins, colistins, tyrocidin, gramicidines, and synthetic analogs and modifications and pharmacologically-active fragments thereof.

Upon collection of the microparticles, a desired range of particle sizes may be directly obtained by sieving. In addition, the particles may be milled, such as by an ultracentrifuge mill. The microparticles are perferably sized less than about 250 microns, more preferably between about 120 and about 250 microns.

The resulting particles are combined with a suitable liquid for administration. The microparticles may be dispersed, e.g. suspended, in other known, suitable liquid vehicles for administration, such as water, dextrose solution, glycerol, or water containing 2% w/v sodium carboxyl-methyl-cellulose 330 (NaCMC) or hydroxypropylmethyl cellulose (HPMC), to increase viscosity to prevent microparticles from settling out of suspension. The particles may be administered to living organisms; including pigs or other mammals and birds, such as chickens or turkeys. For example, somatogenin microparticle formulations may be placed in suspension and injected subcutaneously in the flank of swine. The microparticle formulations may also be injected directly into a bird or administered indirectly into a bird embryo by injection into the air sac of an egg as described in U.S. patent application, Ser. No. 08/068,413, now abandoned (LLY 40), entitled Method for Administering Biological Agents, incorporated herein by reference.

It will further be appreciated by those skilled in the art that the microparticles containing incorporated drugs for release to target cells or tissues may be administered alone or in a mixture with appropriate pharmaceutical diluents, carriers, excipients or adjuvants suitably selected with respect to the intended route of administration and conventional pharmaceutical practices. These inert pharmaceutically acceptable adjuvants are well known in the art. For example, for parenteral injections, dosage unit forms may be utilized to accomplish intravenous, intramuscular or subcutaneous administration, and for such parenteral administration, suitable sterile aqueous or non-aqueous solutions or suspensions, optionally containing appropriate solutes to effect isotonicity, will be employed.

The following specific examples are provided for purposes of illustrating the invention, and no limitations on the invention are intended thereby.

EXAMPLE 1

10% Somatogenin in PLA/PGA (85/15)
Microparticles

Microparticles were prepared using PLA/PGA, 85/15, BPI, and the microparticle preparation technique of solvent evaporation from Dulbecco's phosphate buffered saline (PBS) containing polyvinyl alcohol (PVA). To 250 ml of freshly prepared Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature using magnetic stirring, and the temperature was raised to 45° C. to complete PVA dissolution. The Dulbecco's PBS solution containing PVA was allowed to return to room temperature before use.

1.80 g of PLA/PGA, 85/15, BPI, inherent viscosity of 0.58 dL g in $CHCl_3$ @30° C. ($M_W$=90,900 Daltons, $M_N$=50,100 Daltons), was dissolved in approximately 50 ml of methylene chloride. To this polymer solution was added 0.20 g of air milled somatogenin. The active somatogenin was dispersed to primary particle size using gentle swirling and sonication for approximately one minute. The polymer solution—somatogenin suspension was added to the vortex of the stirred Dulbecco's PBS containing PVA. The rate of stirring was 270–280 RPM. A 400 ml Pyrex beaker and plastic stirring rod with 3-bladed propeller were used to contain and stir the resulting oil-in-water emulsion. This was allowed to continue stirring overnight, resulting in complete evaporation of methylene chloride and the subsequent formation of microspheres, which were recovered using vacuum filtration. The microspheres were placed in a drying dish in a desicator under vacuum to dry. 1.80 g+1.85 g (3.65 g, representing two batches) of dried microparticles were recovered, and sieved to the following mesh cuts:

>60 mesh—trace
60–120 mesh—2.66 g
<120 mesh —0.94 g

Assay of combined product showed a 9.8% w/w (10.2, 9.4, 9.7) loading, as compared to 10% theoretical.

EXAMPLE 2

12.5% Somatogenin in PLA/PGA (85/15) Microparticles

Somatogenin containing microparticles were prepared using PLA/PGA, 85/15, BPI, and the microparticle preparation technique of solvent evaporation from Dulbecco's phosphate buffered saline (PBS) containing polyvinyl alcohol. To 250 ml of Dulbecco's PBS (without $CaCl_2$) was added 1.02 g of Air Products Airvol 205, polyvinyl alcohol to prepare a 0.4% w/v solution of PVA in PBS. The PVA was dispersed in PBS at room temperature, and the temperature raised to 45° C. to facilitate dissolution. The PBS containing PVA solution was allowed to return to room temperature before use.

1.75 g of PLA/PGA, 85/15, BPI, inherent viscosity of 0.58 dL/g in $CHCl_3$ @30° C. ($M_W$=90,900 Daltons, $M_N$=50,100 Daltons), was dissolved in approximately 50 ml of methylene chloride. To this polymer solution was added 0.25 g of air milled somatogenin. The somatogenin was dispersed to primary particle size using gentle agitation and sonication for approximately one minute. The polymer solution somatogenin suspension was added to the vortex of the stirred Dulbecco's PBS containing PVA, and stirring was continued overnight, resulting in complete evaporation of methylene chloride. The resulting microparticles were recovered using vacuum,n filtration and placed in a drying dish in a desicator under vacuum to dry, yielding 1.81 g of dried microparticles, sieved to the following mesh cuts (U.S. Standard):

>60 mesh—none
60–120 mesh—0.96 g
<120 mesh —0.08 g

Assay of the 60–120 mesh cut showed 12.9% w/w somatogenin (12.5% theoretical).

EXAMPLE 3

15% Somatogenin in PLA/PGA (85/15) Microparticles

Microparticles containing somatogenin were prepared using PLA/PGA (85/15) BPI and the microparticle preparation technique of solvent evaporation from Dulbecco's PBS containing polyvinyl alcohol (PVA). To 250 ml of freshly prepared Dulbecco's phosphate buffered saline (PBS) (without $CaCl_2$), was added 1.0 g of Air Products V-205 PVA to prepare a 0.4% w/v solution of PVA in PBS. The PVA was dispersed in the PBS at room temperature, and the temperature was raised to 45° C. to aid dissolution. This solution was allowed to cool to room temperature before use. This solution contained 0.4% w/v PVA in PBS.

1.5 g of PLA/PGA, 85/15, inherent viscosity of 0.58 dL/g in $CHCl_3$ @30° C. ($M_W$=90,900 Daltons, $M_N$=50,100 Daltons), was dissolved in approximately 50 ml of methylene chloride. To this polymer solution was added 0.5 g of micronized somatogenin. The somatogenin was dispersed to primary particle size using gentle agitation and sonication for approximately one minute (at room temperature). The polymer solution/somatogenin suspension was added to the vortex of the stirred Dulbecco's PBS solution containing PVA. The stirring was allowed to continue overnight, allowing the methylene chloride solvent to completely evaporate. The microparticles were recovered using vacuum filtration and were placed in a drying dish in a desiccator under vacuum to dry. 1.84 g of dried microparticles were recovered and were sieved to the following mesh cuts (U.S. Standard):

>60 mesh—0.01 g (discarded)
60–120 mesh—0.86 g
<120 mesh—0.94 g

Repetition of the foregoing process yielded 1.87 g of dried microparticles, which were sieved to the following mesh cuts (U.S. Standard):

>60 mesh—trace (discarded)
60–120 mesh—1.10 g
<120 mesh—0.71 g

These particles assayed as follows:

60–120 mesh=15.7±2.1% loading (somatogenin)
<120 mesh=15.2±0.8% w/w loading (somatogenin)

EXAMPLE 4

25% Somatogenin in PLA/PGA (85/15) Microparticles

Somatogenin containing microparticles were prepared using PLA/PGA, 85/15, BPI, and the microparticle preparation technique of solvent evaporation from Dulbecco's phosphate buffered saline (PBS) containing polyvinyl alcohol (PVA). To 250 ml of Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.52 g of PLA/PGA, 85/15, BPI, inherent viscosity of 0.58 dL/g in $CHCl_3$ @30° C. ($M_W$=90,900 Daltons, $M_N$=50,100 Daltons), was dissolved in approximately 50 ml of methylene chloride. To this polymer solution was added 0.50 g of air milled somatogenin, and the active somatogenin was dispersed to primary particle size using gentle agitation and sonication for approximately one minute. The polymer solution-somatogenin suspension was added to the vortex of the stirred Dulbecco's PBS containing PVA. A 400 ml. Pyrex beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.80 g of dried microparticles were recovered and sieved to the following mesh cuts (U.S. Standard):

>60 mesh—none
60–120 mesh—1.30 g
<120 mesh—0.17 g

Assay of the 60–120 mesh cut showed 24.9% w/w somatogenin loading (25% theoretical).

EXAMPLE 5

25% Somatogenin in PLA/PGA (50/50) Microparticles

Microparticles were prepared using PLA/PGA, 50/50, BPI, and the microparticle preparation technique of solvent evaporation from Dulbecco's phosphate buffered saline (PBS) containing polyvinyl alcohol (PVA). To 250 ml of freshly prepared Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature using magnetic stirring, and the temperature was raised to 45° C. to complete PVA dissolution. The Dulbecco's PBS solution containing PVA was allowed to return to room temperature before use.

1.50 g of PLA/PGA, 50/50, BPI, inherent viscosity of 0.42 dL g in $CHCl_3$ @30° C. ($M_W$=29,000 Daltons, $M_N$=20,000 Daltons), was dissolved in approximately 50 ml of methylene chloride. To this polymer solution was added 0.50 g of air milled somatogenin. The active somatogenin was dispersed to primary particle size using gentle swirling and sonication for approximately one minute. The polymer solution—somatogenin suspension was added to the vortex of the stirred Dulbecco's PBS containing PVA. The rate of stirring was 270–280 RPM. A 400 ml Pyrex beaker and plastic shirring rod with 3-bladed propeller were used to contain and stir the resulting oil-in-water emulsion. This was allowed to continue stirring overnight, resulting in complete evaporation of methylene chloride and the subsequent formation of microspheres, which were recovered using vacuum filtration. The microspheres were placed in a drying dish in a desicator under vacuum to dry. 1.92 g of dried microparticles were recovered, and sieved to the following mesh cuts:

>60 mesh—trace (discard)
60–120 mesh—1.11 g
<120 mesh—0.77 g

EXAMPLE 6

10% Somatogenin in Poly(DL-lactide) Microparticles

Somatogenin containing microparticles were prepared using poly (DL-lactide) PLA/PGA, 85/15, BPI, and the microparticle preparation technique of solvent evaporation from Dulbecco's phosphate buffered saline (FBS) containing polyvinyl alcohol (PVA). To 250 ml of Dulbecco's PDS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.80 g of poly (DL-lactide), BPI, inherent viscosity of 0.34 dL/g in $CHCl_3$ @30° C. ($M_W$=38,300 Daltons, $M_N$=24,300 Daltons), was dissolved in approximately 50 ml of methylene chloride. To this polymer solution was added 0.20 g of air milled somatogenin, and the active somatogenin was dispersed to primary particle size using gentle agitation and sonication for approximately one minute. The polymer solution-somatogenin suspension was added to the vortex of the stirred Dulbecco's PBS containing PVA. A 400 ml beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.68 g of dried microparticles were recovered and sieved to the following mesh cuts (U.S. Standard):

>60 mesh—0.02 g
60–120 mesh—1.36 g
<120 mesh—0.18 g

EXAMPLE 7

10% Somatogenin in Poly(caprolactone) Microparticles

Somatogenin containing microparticles were prepared using poly(caprolactone), BPI, and the microparticle preparation technique of solvent evaporation from Dulbecco's phosphate buffered saline (PBS) containing polyvinyl alcohol (PVA). To 250 ml of Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.80 g of poly(caprolactone) BPI, inherent viscosity of 1.27 dL/g in $CHCl_3$@30° C. [($M_W$=143,000 Dalons, $M_N$=83,000 Daltons),] was dissolved in approximately 50 ml of methylene chloride. To this polymer solution was added 0.50 g of air milled somatogenin, and the active somatogenin was dispersed to primary particle size using gentle agitation and sonication for approximately one minute. The polymer solution-somatogenin suspension was added to the vortex of the stirred Dulbecco's PBS containing FVA. A 400 ml. Pyrex beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.85 g of dried microparticles were recovered and sieved to the following mesh cuts (U.S. Standard):

>60 mesh—trace
60–120 mesh—1.27 g
<120 mesh—0.58 g

EXAMPLE 8

10% Somatogenin in Poly(caprolactone)-Palmitic Acid (1%) Microparticles

Somatogenin containing microparticles were prepared using poly(caprolactone) and the microparticle preparation technique of solvent evaporation from Dulbecco's phosphate buffered saline (PBS) containing polyvinyl alcohol (PVA). To 250 ml of Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.78 g of polycaprolactone, low molecular weight, Polysciences, was dissolved in approximately 50 ml of methylene chloride. To this polymer solution was added 0.02 g of palmitic acid. To this solution of polymer-fatty acid was added 0.20 g of air milled somatogenin, and the active somatogenin was dispersed to primary particle size using gentle agitation and sonication for approximately one minute. The polymer solution-somatogenin suspension was added to the vortex of the stirred Dulbecco's PBS containing PVA. A 400 ml. Pyrex beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.89 g of dried microparticles were recovered and sieved to the following mesh cuts (U.S. Standard):

>60 mesh—0.03 g
60–120 mesh—1.15 g
<120 mesh—0.74 g

EXAMPLE 9

10% Somatogenin in Poly(caprolactone)-Palmitic acid (5%) Microparticles

Somatogenin containing microparticles were prepared using poly(caprolactone), and the microparticle preparation technique of solvent evaporation from Dulbecco's phosphate buffered saline (PBS) containing polyvinyl alcohol (PVA). To 250 ml of Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.70 g of poly(caprolactone), low molecular weight, Polysciences, was dissolved in approximately 50 ml of methylene chloride. To this polymer solution was added 0.10 g of palmitic acid. To this polymer-fatty acid solution was added 0.20 g of air milled somatogenin, and the active somatogenin was dispersed to primary particle size using gentle agitation and sonication for approximately one minute. The polymer solution-somatogenin suspension was added to the vortex of the stirred Dulbecco's PBS containing PVA. A 400 ml. Pyrex beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.93 g of dried microparticles were recovered and sieved to the following mesh cuts (U.S. Standard):

>60 mesh—0.01 g
60–120 mesh—1.06 g
<120 mesh—0.82 g

EXAMPLE 10

10% Somatogenin in Poly(caprolactone)-Palmitic acid 10% Microparticles

Somatogenin containing microparticles were prepared using poly(caprolactone), and the microparticle preparation technique of solvent evaporation from Dulbecco's phosphate buffered saline (PBS) containing polyvinyl alcohol (PVA). To 250 ml of Dulbecco's PBS (without $CaCl_2$) was added 1.0 g of Air Products Airvol 205 polyvinyl alcohol to prepare a 0.4% w/v solution of PVA in PBS. The PVA was dispersed in PBS at room temperature and the temperature raised to 45° C. to aid dissolution. This PVA containing solution was returned to room temperature before use.

1.60 g of poly(caprolactone), low molecular weight, Polysciences was dissolved in approximately 50 ml of methylene chloride. To this polymer solution was added 0.20 g of palmitic acid. To this solution of polymer-fatty acid was added 0.20 g of air milled somatogenin, and the active somatogenin was dispersed to primary particle size using gentle agitation and sonication for approximately one minute. The polymer solution-somatogenin suspension was added to the vortex of the stirred Dulbecco's PBS containing PVA. A 400 ml. Pyrex beaker and a plastic 3-bladed stirrer and shaft were used to contain and agitate the oil-in-water emulsion. Stirring continued overnight, resulting in complete evaporation of methylene chloride. The resulting microparticles were recovered using vacuum filtration and placed in a drying dish in a desicator under vacuum to dry. 1.91 g of dried microparticles were recovered and sieved to the following mesh cuts (U.S. Standard):

>60 mesh—trace
60–120 mesh—1.17 g
<1.20 mesh—0.69 g

EXAMPLE 11

Effect of Somatogenin Concentration on Payout Profile

The microparticles prepared in accordance with the previous examples were used to determine the effect of somatogenin (LY293404) concentration in different PLA/PGA microparticle concentrations. Payout characteristics were measured by urinary urea nitrogen excretion and serum growth hormone levels in finishing swine. The microparticle formulations were placed in suspension, using 2% W/V sodium carboxyl-methyl-cellulose 330 (NaCMC) in Nanopure II purified water. The suspension was injected subcutaneously in the flank. The following treatment (Trt) materials were prepared:

Trt A: water as control;

Trt B: 5% Somatogenin PLA/PGA (85:15) microparticles (60–120 mesh, MW=90,900, Viscosity=0.58 dL/g in CHCl3 @30° C.) suspended in water containing 2% w/v NaCMC 330 to give a dose of 42 mg somatogenin/animal.

Trt C: 10% Somatogenin PLA/PLG (85:15) microparticles (60–120 mesh, MW=90,900, Viscosity=0.58 dL/g in CHCl3 @30° C.) suspended in water containing 2% w/v NaCMC 330 to give a dose of 42 mg somatogenin/animal.

TrT D: 25% Somatogenin PLA/PLG (85:15) microparticles (60–120 mesh, MW=90,900, Viscosity=0.58 dL/g in CHCl3 @30° C.) suspended in water containing 2% w/v NaCMC 330 to give a dose of 42 mg somatogenin/animal.

Figure 1:
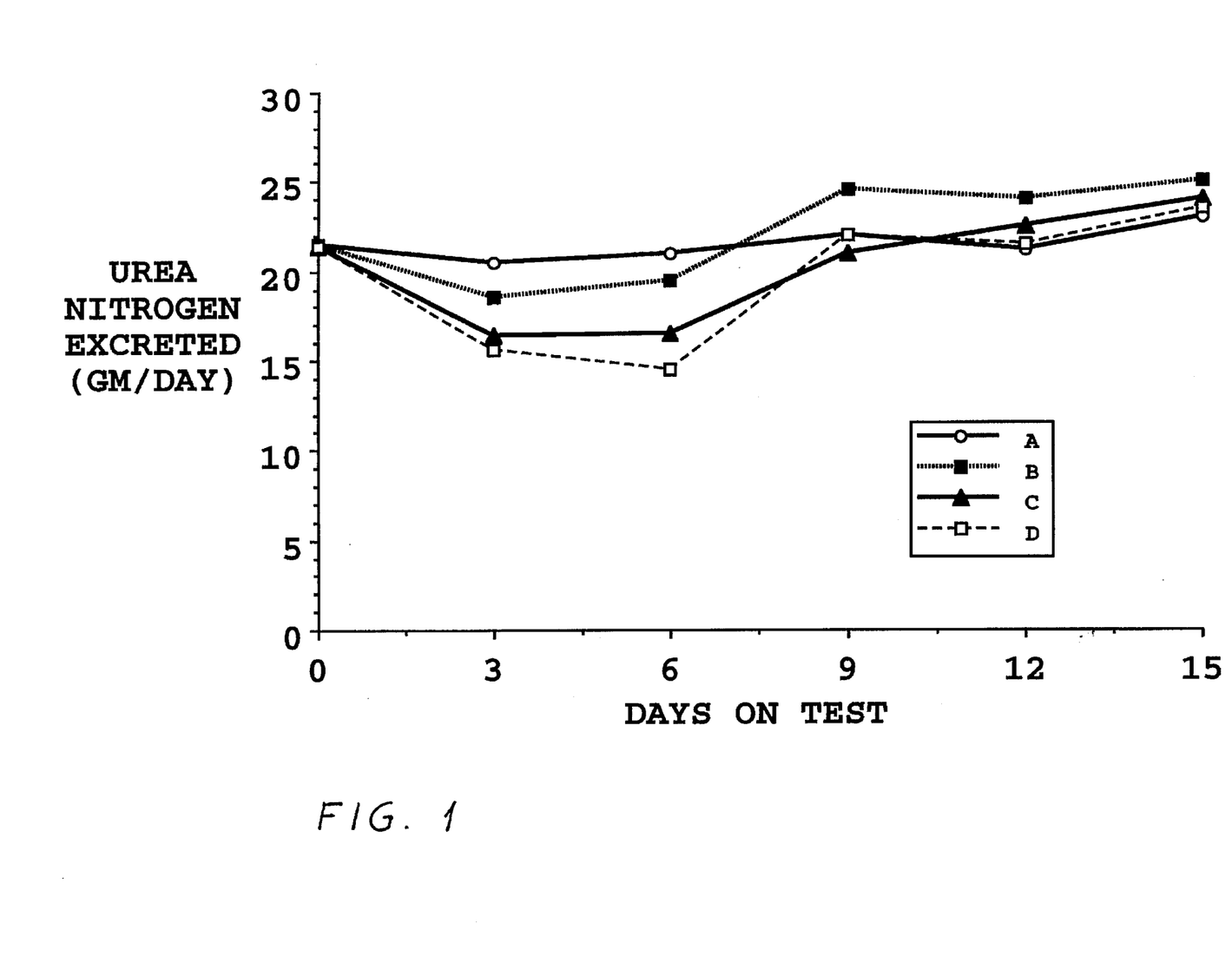
FIGS. 1–4 are graphs representing in vivo studies in swine demonstrating biological consequences of somatogenin controlled release from microparticles.
Figure 2:
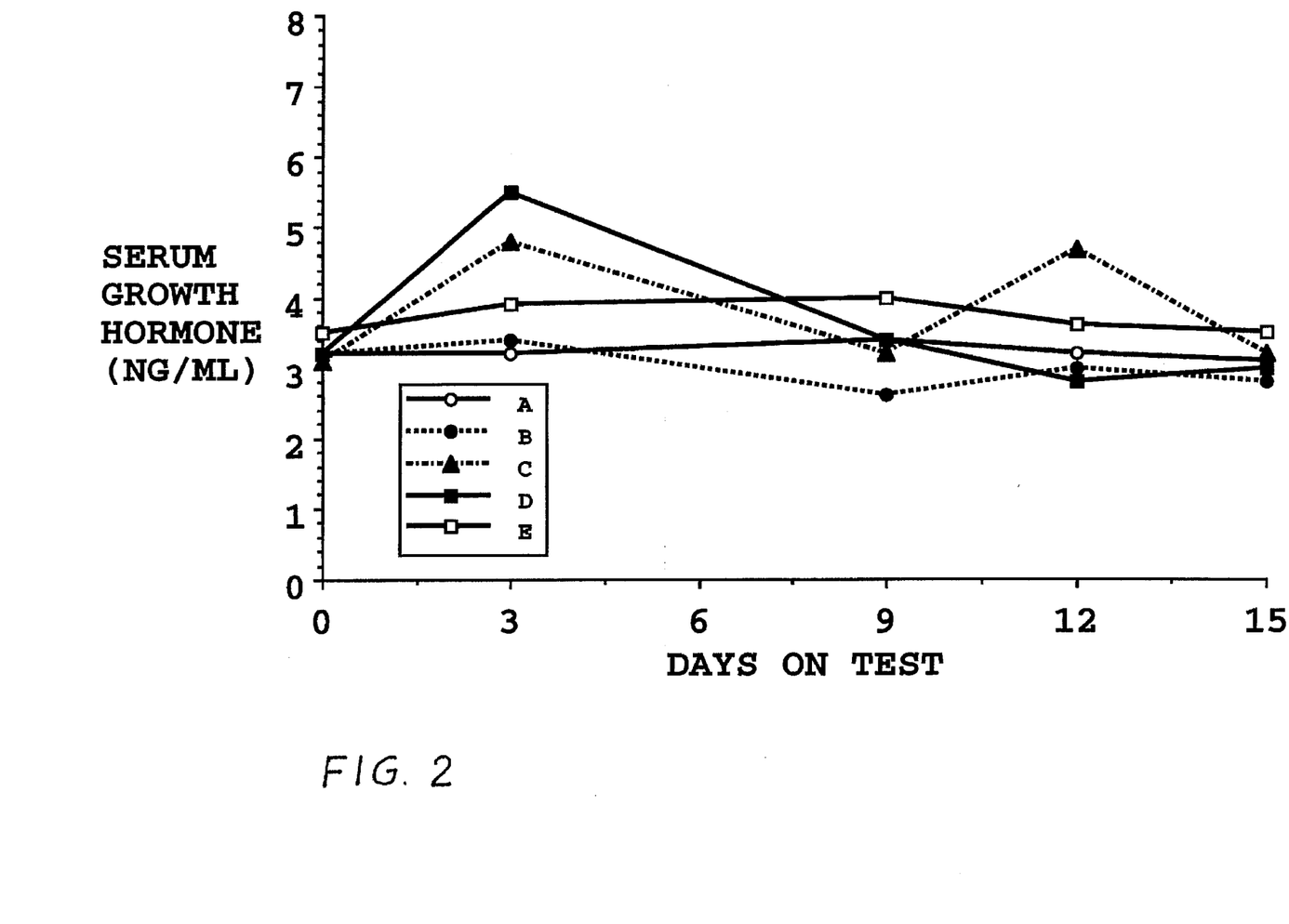

The results of this study demonstrate the efficacy of the microparticles for prolonged release of a contained peptide. Urinary nitrogen reduction is a measurement of growth hormone which is stimulated by somatogenin release from microparticles. As shown in FIG. 1, there was a reduction in urinary urea nitrogen excreted in all microparticle treated pigs during the first six days of treatment. The reduction was the greatest for the highest loaded (25%) microparticles, and lowest for the lowest (5%) loaded microparticles. FIG. 2 shows the direct measurement of serum growth hormone for microparticle treated pigs, further evidencing the sustained release from the microparticles of the somatogenin over time. The vertical bars in the figures represent the relative standard deviations.

EXAMPLE 13

Payout Profiles of Somatogenin with Different PLA/PGA Microparticle Formulations The microparticles prepared in accordance with the previous examples were used to determine the payout characteristics of somatogenin (LY293404) when administered in different PLA/PLG microparticle formulations as measured by urinary urea nitrogen excretion and serum growth hormone levels in finishing swine. The microparticle formulations were placed in suspension, using 2% W/V sodium carboxyl-methyl-cellulose 330 (NaCMC) in Nano-pure II purified water. The suspension was injected subcutaneously in the flank. The following treatment (Trt) materials were prepared:

Trt A: water as control;

Trt B: Somatogenin (3 micrograms/kg/day injected twice per day) as positive control Trt C: 11.7% Somatogenin PLA/PLG (50:50) microparticles (60–120 mesh, MW=60,700) suspended in water containing 2% w/v NaCMC 330 to give a dose of 22.68 mg somatogenin/animal.

Trt D: 11.4% Somatogenin PLA/PLG (50:50) microparticles (60–120 mesh, MW=29,000) suspended in water containing 2% w/v NaCMC 330 to give a dose of 7.56 mg somatogenin/animal.

11.4% Somatogenin PLA/PLG (50:50) microparticles (60–120, mesh, MW=29,000) suspended in water containing 2% w/v NaCMC 330 to give a dose of 22.68 mg somatogenin/animal.

Trt F: 13.6% Somatogenin PLA/PLG (85:15) microparticles (60–120 mesh, MW=90,900) suspended in water containing 2% w/v NaCMC 330 to give a dose of 7.56 mg somatogenin/animal.

Trt G: 13.6% Somatogenin PLA/PLG (85:15) microparticles (60–120 mesh, MW=90,900) suspended in water containing 2% w/v NaCMC 330 to give a dose of 22.68 mg somatogenin/animal.

Figure 3:
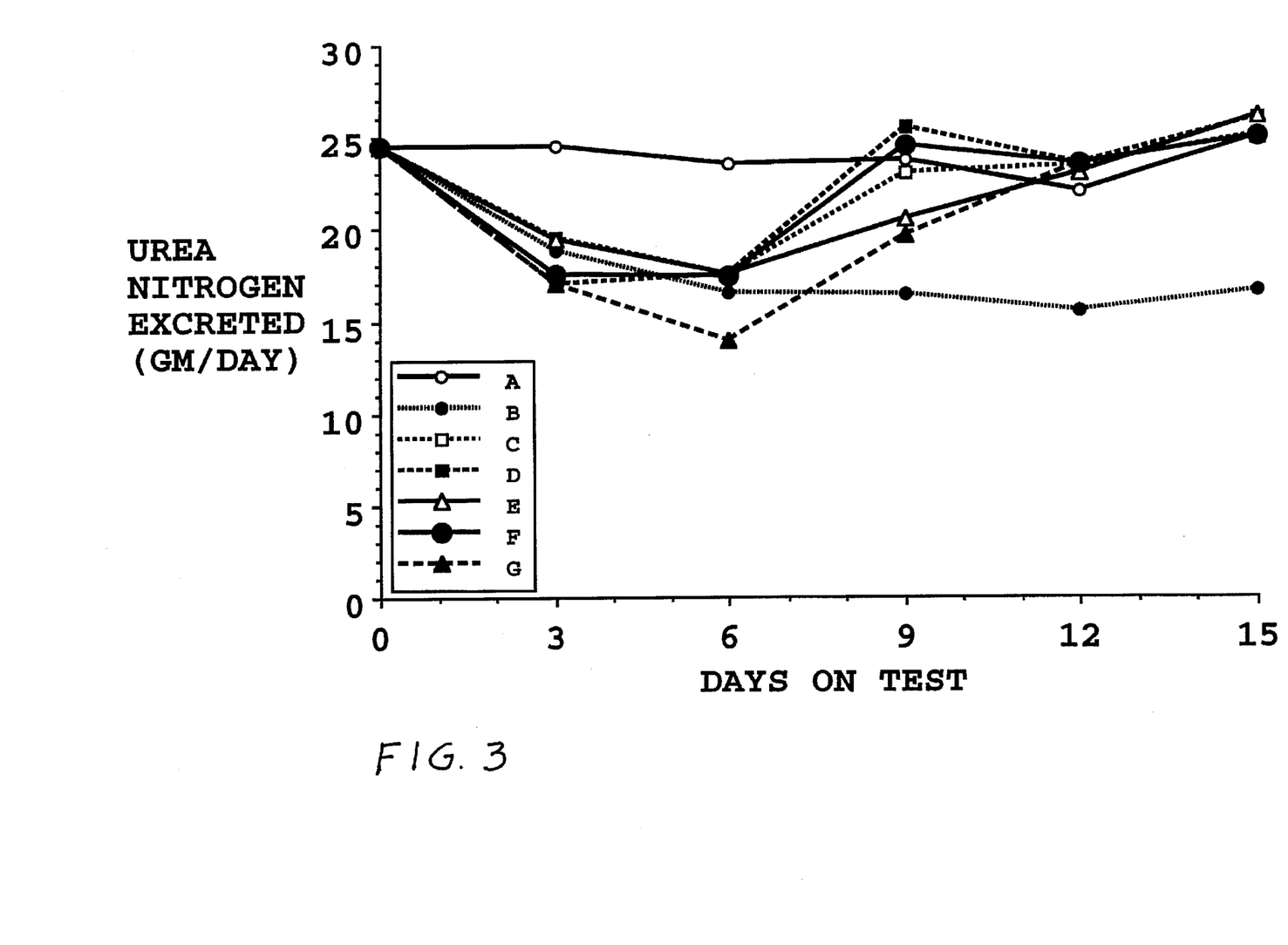
Figure 4:
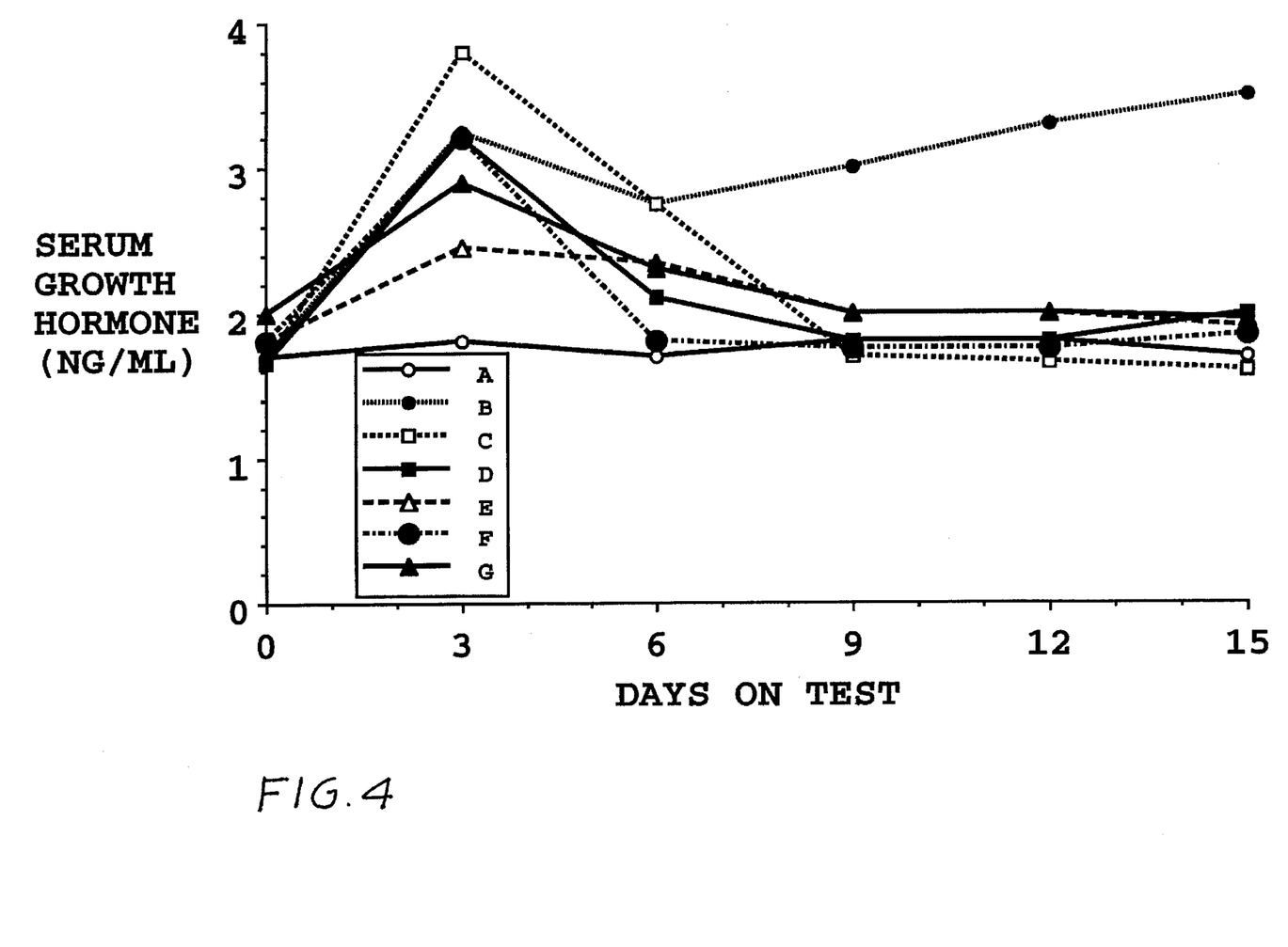

As shown in FIGS. 3 and 4, there was a reduction in urinary urea excretion and an elevation in serum GH levels in the somatogenin injected (BID) barrows at all time periods for 15 days. Urinary urea nitrogen excretion was less and serum GH levels were elevated in all microparticle treated pigs during the first 6 days of treatment. Urinary urea nitrogen excretion and serum GH levels returned to baseline levels at approximately 9 days after treatment.

EXAMPLE 13

In Ovo Injection Studies

Test materials for in ovo injection studies, using the products of the previous Examples were prepared as follows:

Trt A: water as control;

Trt B: micronized somatogenin dispersed in 50 ml purified water to yield a concentration of 60 µg somatogenin per 100 µl water;

Trt C: micronized somatogenin dispersed in 50 ml purified water to yield a concentration of 600 µg somatogenin per 100 µl water;

Trt D: microparticles (Somatogenin PLA/PGA, 60–120 mesh) dispersed in 50 ml of 2% w/v sodium carboxy methyl cellulose (NaCMC 330) to yield a suspension containing microparticles equivalent to 60 µg somatogenin/100 µl (amount dispersed on loading);

Trt E: microparticles (Somatogenin PLA/PGA, 60–120 mesh) dispersed in 50 ml of 2% w/v NaCMC 330 to yield a suspension containing microparticles equivalent to 600 µg somatogenin/100 µl (amount dispersed based on loading); and Trt F: blank microparticles (PLA/PGA, 60–120 mesh) dispersed in 50 ml of 2% w/v NaCMC 330, approximately equivalent to high dose somatogenin PLA/PGA (Trt E).

Upon injection of the foregoing materials into the air cells of eggs, the particles migrated to the bottoms of the eggs, typically within a few hours. No decrease in hatchability was noted for any treatment.

While the invention has been described in detail in the foregoing description, the same is to be considered as illustrative and not restrictive in character, it being understood that only the preferred embodiments have been shown and described, and that all changes and modifications that come within the spirit of the invention are desired to be protected.

---

I claim:

1. A biocompatible, biodegradable composition, comprising: microparticles having polyester matrices; and from about 5% to about 25% by weight of a biologically active, water-soluble polypeptide dispersed throughout the matrix, the polypeptide selected from the group consisting of growth hormone releasing factor, synthetic analogs of growth hormone releasing factor, pharmacologically active fragments thereof and somatogenin, wherein the biodegradable composition contains no polypeptide which is destabilized, or inactivated and contains no polypeptide destruction products.

2. The composition of claim 1 wherein the polyester is a polymer selected from the group consisting of poly (caprolactone), a polymer of lactic acid, a copolymer of lactic acid add glycolic acid, a mixture of such polymers, a mixture of such copolymers, or a mixture of such polymers and copolymers.

3. The composition of claim 2 wherein the ratio of lactide units to glycolide units is from about 50:50 to about 100:0.

4. The biocompatible, biodegradable microparticle composition of claim 3 wherein the ratio of lactic acid to glycolic acid in the polylactide is about 85:15 in $CHCL_3$ at 30° C.

5. The biocompatible, biodegradable microparticle composition of claim 3 wherein the ratio of lactic acid to glycolic acid in the polylactide is about 50:50 in $CHCL_3$ at 30° C.

6. The biocompatible, biodegradable microparticle composition of claim 3 wherein the polylactide is a polymer of lactide alone in $CHCL_3$ at 30° C.

\* \* \* \* \*